United States Patent
Baldus et al.

(10) Patent No.: US 10,709,331 B2
(45) Date of Patent: Jul. 14, 2020

(54) AUTOMATIC TRANSFER AND IDENTIFICATION OF MONITORED DATA WITH HIERARCHICAL KEY MANAGEMENT INFRASTRUCTURE

(75) Inventors: Heibert Baldus, Aachen (DE); David P. L. Simons, Veldhoven (NL); Karin Klabunde, Bochum (DE); Oscar Garcia Morchon, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1894 days.

(21) Appl. No.: 12/375,419

(22) PCT Filed: Jul. 27, 2007

(86) PCT No.: PCT/US2007/074544
§ 371 (c)(1),
(2), (4) Date: Jan. 28, 2009

(87) PCT Pub. No.: WO2008/014432
PCT Pub. Date: Jan. 31, 2008

(65) Prior Publication Data
US 2009/0264712 A1    Oct. 22, 2009

Related U.S. Application Data

(60) Provisional application No. 60/820,613, filed on Jul. 28, 2006, provisional application No. 60/827,496, filed on Sep. 29, 2006.

(51) Int. Cl.
*A61B 5/00* (2006.01)
*H04L 29/06* (2006.01)
(Continued)

(52) U.S. Cl.
CPC .......... *A61B 5/0002* (2013.01); *A61B 5/0028* (2013.01); *H04B 13/005* (2013.01);
(Continued)

(58) Field of Classification Search
CPC ..... A61B 5/117; A61B 5/0002; A61B 5/0028; Y02D 30/40; H04L 2209/805;
(Continued)

(56) References Cited

U.S. PATENT DOCUMENTS 5,914,701 A *  6/1999  Gersheneld et al. ......... 345/156
6,198,394 B1 * 3/2001  Jacobsen et al. .......... 340/573.1
(Continued)

FOREIGN PATENT DOCUMENTS

EP    1587017 A2    10/2005
GB    2259772 A     3/1993
(Continued)

OTHER PUBLICATIONS

Ramkumar, M.; Memon, N.; Simha, R., "A hierarchical key pre-distribution scheme," Electro Information Technology, 2005 IEEE International Conference on, pp. 6, May 22-25, 2005, doi: 10.1109/EIT.2005.1626994.*

(Continued)

*Primary Examiner* — Lynsey C Eiseman
*Assistant Examiner* — Amanda L Steinberg (57) ABSTRACT

A measurement device (14) includes a measuring unit (42) for obtaining health related parameters of a patient (12), and a body-coupled communication unit (40) for sending at least measurement results. An identification device (20), associated with the patient, includes a body-coupled communication unit (26) for receiving and sending out the measurement results. A gateway device (72) includes a body-coupled communication unit (78) for receiving patient's measurement results. Additionally, a hierarchical relational deployment model (100) facilitates grouping wireless devices in a healthcare environment into subgroups based on relationships between the devices, and a hierarchical key pre-distribution scheme (110) permits distribution of unique (Continued)

keying material for security domains of respective groups of devices, prior to deploying the devices in a healthcare network. Devices can then execute a handshake protocol by which they identify their deepest common node in the deployment model (100), and employ keying material assigned to that nodes group in the pre-distribution scheme (110) to facilitate granular communication security.

9 Claims, 6 Drawing Sheets

(51) Int. Cl.
*H04L 9/08* (2006.01)
*H04W 12/04* (2009.01)
*H04B 13/00* (2006.01)
*H04L 29/08* (2006.01)
*H04W 84/18* (2009.01)
*H04W 12/00* (2009.01)

(52) U.S. Cl.
CPC .......... *H04L 9/0836* (2013.01); *H04L 63/064* (2013.01); *H04L 67/12* (2013.01); *H04W 12/04* (2013.01); *H04L 2209/805* (2013.01); *H04L 2209/88* (2013.01); *H04W 12/00503* (2019.01); *H04W 12/00508* (2019.01); *H04W 84/18* (2013.01); *Y02D 30/40* (2018.01)

(58) Field of Classification Search
CPC . H04L 2209/88; H04L 9/0836; H04L 63/064; H04B 13/005
See application file for complete search history.

(56) References Cited

U.S. PATENT DOCUMENTS

| | | | |
|---|---|---|---|
| 6,255,951 B1* | 7/2001 | De La Huerga | 340/573.1 |
| 6,263,435 B1 | 7/2001 | Dondeti et al. | |
| 6,346,886 B1* | 2/2002 | De La Huerga | 340/573.1 |
| 6,441,721 B1 | 8/2002 | Tajima et al. | |
| 6,450,953 B1 | 9/2002 | Place et al. | |
| 6,957,107 B2* | 10/2005 | Rogers et al. | 607/60 |
| 7,684,754 B2* | 3/2010 | Glass et al. | 455/41.2 |
| 7,965,845 B2 | 6/2011 | Baldus et al. | |
| 8,798,015 B2 | 8/2014 | Herrmann et al. | |
| 9,419,951 B1* | 8/2016 | Felsher | H04L 9/0825 |
| 2002/0065685 A1* | 5/2002 | Sasaki et al. | 705/3 |
| 2002/0084904 A1* | 7/2002 | De La Huerga | 340/573.1 |
| 2003/0125017 A1* | 7/2003 | Greene et al. | 455/414 |
| 2003/0158707 A1 | 8/2003 | Doi | |
| 2003/0229514 A2 | 12/2003 | Brown | |
| 2004/0122315 A1* | 6/2004 | Krill | 600/437 |
| 2004/0133242 A1 | 7/2004 | Chapman et al. | |
| 2005/0101843 A1 | 5/2005 | Quinn et al. | |
| 2005/0101844 A1* | 5/2005 | Duckert et al. | 600/300 |
| 2005/0278194 A1* | 12/2005 | Holland et al. | 705/2 |
| 2006/0031378 A1* | 2/2006 | Vallapureddy et al. | 709/208 |
| 2006/0064323 A1* | 3/2006 | Alleckson et al. | 705/2 |
| 2006/0066449 A1 | 3/2006 | Johnson | |
| 2006/0224048 A1* | 10/2006 | Devaul et al. | 600/300 |
| 2006/0252999 A1* | 11/2006 | Devaul et al. | 600/300 |
| 2007/0063850 A1* | 3/2007 | Devaul et al. | 340/573.1 |
| 2007/0273504 A1* | 11/2007 | Tran | 340/539.12 |
| 2008/0191866 A1* | 8/2008 | Falck et al. | 340/539.12 |

FOREIGN PATENT DOCUMENTS

| | | | | |
|---|---|---|---|---|
| JP | 2003175139 A | | 6/2003 | |
| JP | 2006053722 A | | 2/2006 | |
| JP | 2006110180 A | | 4/2006 | |
| WO | WO 0147418 A1 | * | 7/2001 | |
| WO | WO-2005114524 A2 | * | 12/2005 | G06F 19/3418 |
| WO | 2006035351 A2 | | 4/2006 | |
| WO | 2006051464 A1 | | 5/2006 | |
| WO | 2006064397 A2 | | 6/2006 | |

OTHER PUBLICATIONS

Blundo, C., et al.; Perfectly-Secure Key Distribution for Dynamic Conferences; 1992; Crypto: 471-486.

Chuang, P-J., et al.; A Scalable Grouping Random Key Predistribution Scheme for Large Scale Distributed Sensor Networks; 2005; Proc. of ICITA; vol. 2:535-540.

Morchon, O. G., et al.; Resource-Efficient Security for Medical Body Sensor Networks; 2006; IEEE Trans. on Intl. Workshop on Wearable and Implantable Body Sensor Networks; pp. 80-83.

Song, W. J., et al.; Privacy and Security Control Architecture for Ubiquitous RFID Healthcare System in Wireless Sensor Networks; 2006; IEEE Trans. on Intl. Conf. on Consumer Electronics; pp. 239-240.

Chen, X., et al.; An Efficient Key Management Scheme in Hierarchical Sensor Networks; 2005; IEEE Mobile Adhoc and Sensor Systems Conference; pp. 846.

\* cited by examiner

AUTOMATIC TRANSFER AND IDENTIFICATION OF MONITORED DATA WITH HIERARCHICAL KEY MANAGEMENT INFRASTRUCTURE

The present application relates to remote patient monitoring arts. It finds particular application in relation to self-taken medical and health-related measurements and will be described with particular reference thereto. It is to be appreciated that the following will find application in conjunction with patient monitoring, at home, in retirement communities, assisted living, pharmacies, community centers, and the like, and in preventive health monitoring applications.

The outpatient or remote health care management system typically connects chronically ill patients and health care providers via an interactive health care communication platform. The patients use the measurement devices which are installed in their homes to measure vital signs such as blood pressure, heart rate, blood oxygen, weight, and the like. The measurement devices wirelessly transmit the patient's biometric data via secured signal connection links to the gateway device. The gateway device, for example, processes the patient's data and forwards it to the monitoring center. Thus, the health care providers can monitor the patient's health and, for example, intervene if one of the vital sign measurements falls outside the normal range.

While the remote health care management system functions well for a single patient at one location, many of the patients are elderly and their spouses also have medical problems. If the elderly couple shares the medical monitoring device, it is problematic for the remote health care management system to distinguish whose measurements are being taken. Therefore, typically, each patient is assigned a separate, dedicated medical device, for example, a weight scale or a blood pressure device. Every measurement that is taken is attributed to the one known, designated user, the identity of whom is assumed. Other users, e.g. a spouse, are prohibited to use the device because their use would lead to invalid measurements in the collected data. The purchase of two medical monitors for a single home of two people doubles the costs, which to date are significant.

Another problem arises with a requirement to secure the patient's data. Because of privacy regulations, no patient identifiable data can be disclosed to unauthorized parties. Many wireless technologies provide security measures to stay in compliance, such as an encryption. While working well in such wireless communications, the encryption is not a perfect measure as it can be broken into.

Moreover, because of the safety concerns, the home measurement devices, e.g. weight scales, are powered by the batteries. Current wireless technologies are typically consume high power which leads to frequent change of the batteries, thus resulting in increased costs and inconvenience to the patient.

Additionally, wireless vital sign sensors are increasingly deployed for health monitoring, both at hospital and at home. Security and privacy is increasingly important for wireless systems, and especially in the medical domain. Security is a desirable feature for such systems in order to both ensure patient safety and privacy, and to comply with legal requirements in healthcare such as HIPAA in U.S.A., etc. Management of encryption keys is therefore desirable to enable medical body sensor networks (BSN) security, since it provides and manages the cryptographic keys to enable further security services, such as authentication, confidentiality and integrity. Current key management solutions for wireless hospitals, home monitoring and wireless sensor networks in general are based on the pre-distribution of some keying material (e.g., key pre-distribution schemes, (KPS)). Those schemes aim at static networks, whereas hospital BSNs and home BSNs are mobile wireless sensor networks (mobile WSNs). A desirable aspect of security and privacy in medical BSNs is the provision of a simple and consistent key distribution scheme (KDS) that guarantees hospitals a secure configuration and deployment of their BSN security system. However mobile WSNs lacks of satisfactory solutions involving KPS, as the scalability and resiliency of these schemes is limited.

The present application provides new and improved methods and apparatuses which overcome the above-referenced problems and others.

In accordance with one aspect, a system for monitoring health related parameters of a patient is disclosed. A measurement device includes a measuring unit for obtaining health related parameters of a patient, and a body-coupled communication unit for sending at least the measurement results. An identification device, associated with the patient, includes a body-coupled communication unit for receiving and sending the measurement results. A gateway device includes a body-coupled communication unit for receiving the patient's measurement results.

In accordance with another aspect, a measurement device, which is intermittently used by at least one patient, is disclosed. A measuring unit measures a health related parameter of the patient. A body-coupled communication unit transmits in a body-coupled communications format a memory packet including at least a value of the measured health related parameter to an identification device carried by the patient whose health related parameter is measured.

In accordance with another aspect, a patient identification device is disclosed. A measurement memory stores health related parameter measurements. A patient identification code memory stores a patient identification code. A body-coupled communication unit communicates via body-coupled communications with a measurement device which a patient has closely approached or touched, receives at least health related parameter measurements by body-coupled communications from the measuring device, which the patient has closely approached or touched, for storage in the measurement memory, and sends the stored health related parameter measurements and the patient identification code by body-coupled communications to a gateway device when the patient closely approaches or touches the gateway device.

In accordance with another aspect, a method for monitoring health related parameters of a patient is disclosed. A health related parameter of the patient is measured with a measurement device. The measurement results are communicated from the measurement device, via body-coupled communication, to an identification device carried by the patient. The measurement results are communicated from the identification device to a gateway device via body-coupled communication.

In accordance with another aspect, a system for monitoring health related parameters of each of a plurality of patients is disclosed. A measurement device includes a measuring unit for obtaining a health related parameter of each of the plurality of patients, and a body-coupled communication unit for communicating the health related parameter measurement. To each patient, a separate, dedicated identification device is assigned, which includes an electronic patient identification code memory for storing a patient identification code, a body-coupled communication unit for communicating at least the patient identification code and the health related parameter measurement, and a measurement memory for storing the received health related parameter measurements. A gateway device receives the measurements and patient identification codes communicated from the patient identification device In accordance with other aspects, patient identification devices, measurement devices, and gateway devices for use in the foregoing systems and method are provided.

In accordance with another aspect, a method of hierarchical security management includes generating an L-level hierarchical relational deployment model (HRDM) including a tree structure of nodes representing respective devices in a healthcare communication network, and generating multi-level hierarchical key pre-distribution scheme (HKPS) and assigning unique keying material to each of a plurality of levels in the HKPS. The method further includes pre-distributing the keying material to the devices in respective levels of the HKPS, and deploying the devices in the healthcare communication network.

One advantage is that the results of patient's measurements are communicated securely by a very short range body-coupled communication link thus eliminating the need of the wireless connection.

Another advantage resides in scalable and granular levels of security provided by the HDMS and HKPS models and systems.

Another advantage resides in the ability to employ any of a number of different types of keying material.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
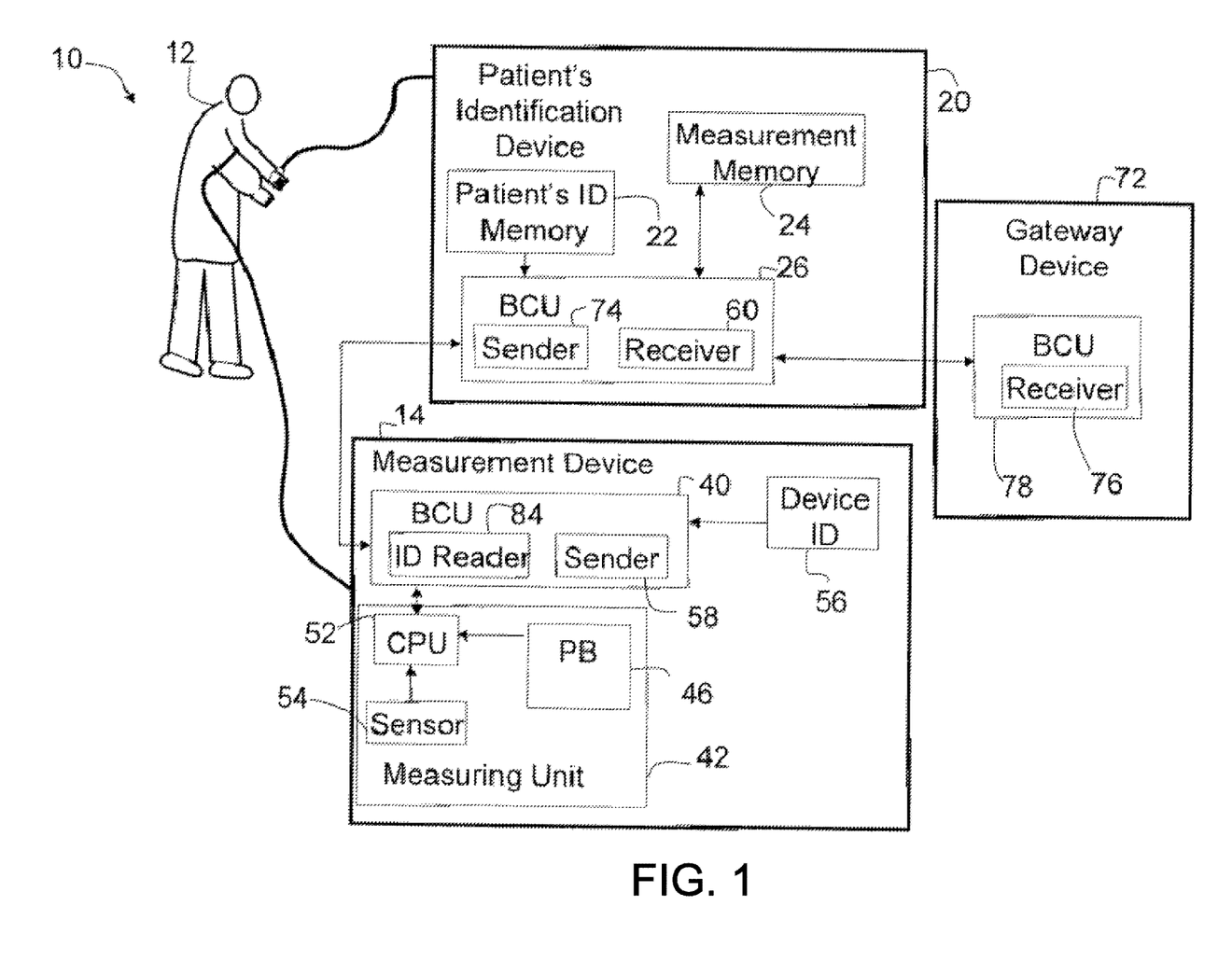
FIG. 1 is a diagrammatical illustration of a patient monitoring system.

With reference to FIG. 1, in a patient monitoring system 10, periodic measurements, such as temperature, blood pressure, weight, and the like, are taken from one or more patients 12 using a measurement device 14 which may include a medical probe. The patient monitoring system can be employed, for instance, in a patient's home or a remote healthcare environment. Additionally or alternatively, the monitoring system is employed in a hospital, institutional setting, or the like. Each patient 12 wears a patient's identification device 20 which communicates via body-coupled communication (BCC) with the measurement device 14. The patient's identification device 20 includes at least a unique patient's identifier (ID) stored in a patient's ID memory 22 and a measurement memory 24. In one embodiment, the unique patient identifier allows relating the measurement results to the specific patient. Of course, it is also contemplated that more information can be stored in the patient's identification device 20, for example, name, anamnesis, diagnosis, therapy and the like.

Each identification device 20 is attached to the patient 12 or patient's body as wrist or leg bands, badges, implants or the like. Alternatively, the identification device 20 is a non-contact device and is attached in a close proximity, e.g. about 10 cm or so, of the patient's body. Such identification device does not need skin contact and can be worn in the shirt pocket. The identification device can take the form of any object or device that is commonly carried by patients on or near their persons, for example, the device can be incorporated into decorative devices or apparel, such as wristbands, watches, necklaces, anklets, etc.

Each identification device 20 includes a first or patient body-coupled communication unit (BCU) 26. The first BCU 26 utilizes a near-field body communication technology, which is based on capacitive coupling and well known in the art, to send and receive the information. The measurement device 14 includes a second or measurement device body-coupled communication unit (BCU) 40 and a measuring unit 42. Typically, the patient activates the measurement device 14 by an activating means such as a switch, pushbutton (PB) 46, or other components commonly used to turn electrical devices on and off. It is also contemplated that the measurement device 14 can be activated when the patient takes the medical measurement device 14 in his hand or touches the measurement device 14.

The measuring unit 42 typically includes a central processing unit (CPU) 52, and optionally a sensor 54. In one embodiment, the measuring unit 42 includes a user interface for manual input of data. The measurement device 14 takes the measurement via the sensor 54 or user interface and, in one embodiment, attaches a time stamp to the measurement. The measurement result along with a device ID 56 is sent via a sender 58 of the measurement device BCU 40 and a receiver 60 of the patient's identification device BCU 26 to the measurement memory 24. The measurement result at least includes the measurement values. In one embodiment, the measurement result includes other parameters such as date, time, type of the measurement device used, and other. Optionally, the measuring unit 42 includes a memory in which the measurements are stored for future communication.

Figure 2:
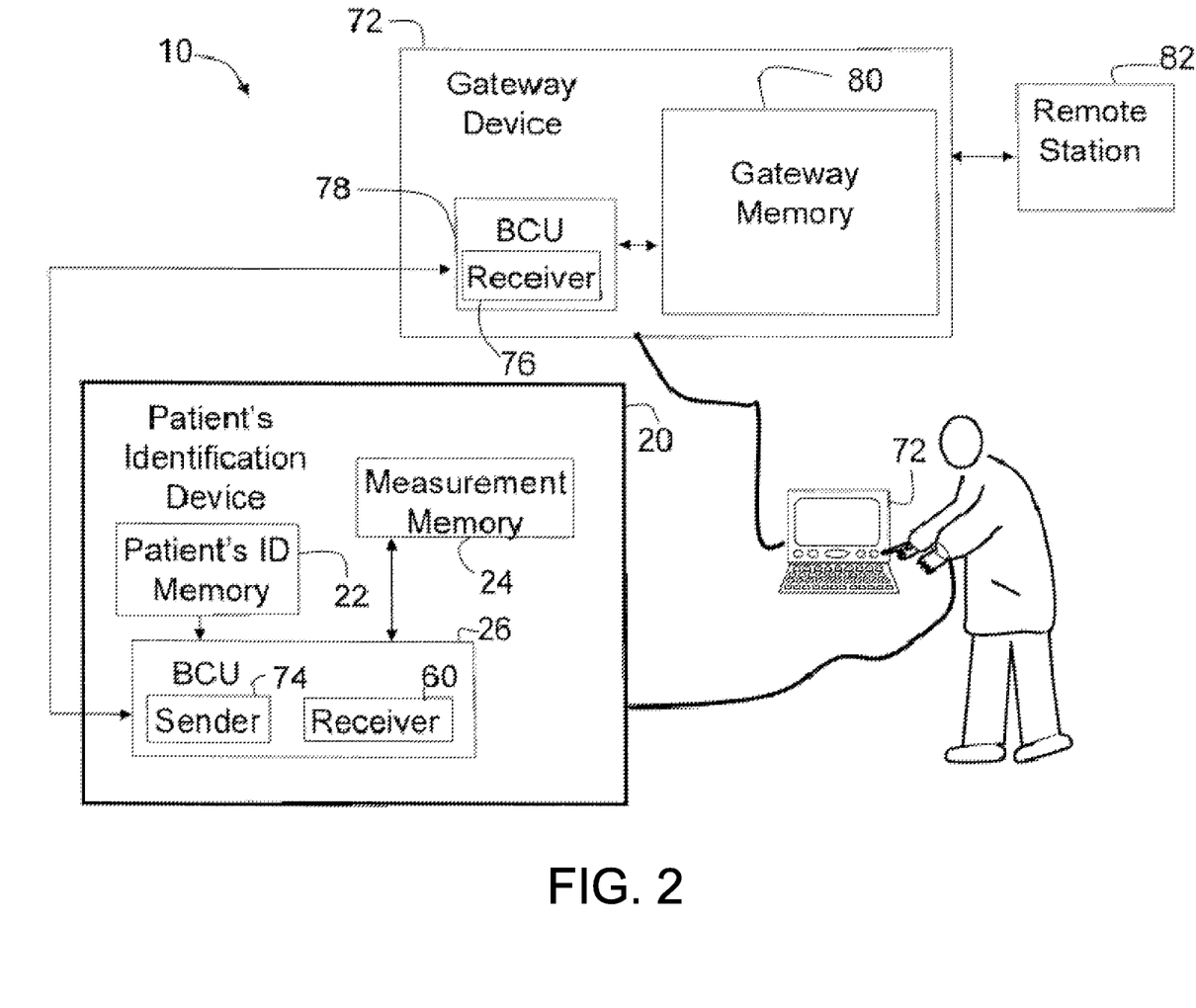
FIG. 2 is a diagrammatical illustration of a detail of a patient monitoring system.

With continuing reference to FIG. 1 and further reference to FIG. 2, after the measurement is taken, the patient returns to a data input area, such as a gateway device 72. More specifically, the patient communicates with the gateway device 72 by touching the gateway device such as a television remote control, television set, a personal computer, set top box, and the like, via the body-coupled communications, e.g. a sender 74 of the patient's identification device 20 and a receiver 76 of a gateway device or third body-coupled communication unit (BCU) 78. The measurement result and the measurement device ID is securely transferred to the gateway device 72, for example, as one message or a packet of data. The third BCU 78 stores the results in a gateway memory 80 and makes the results available to local and remote applications. From the gateway memory 80, the measurement results can be uploaded to broadband internet or dial-up phone connection to a remote station 82, as known in the art.

In this manner, the wireless communication link between the measurement device and the gateway device is replaced by a number of very short range body-coupled communication links and a secured measurement memory, which altogether provides secure communications with minimal power consumption.

In one embodiment, the measurement results are sent to the gateway device 72 along with the patient's ID. For example, the activating means 46 triggers an ID reader 84 of the measurement device BCU 40 which starts looking for identification devices such as the patient's identification device 20. When the measurement device is touching or proximate to the patient, the patient's ID is withdrawn from the patient's ID memory 22 and sent to the measurement device 14 by the sender 74 which is integrated with the patient's BCU 20. If the ID reader 84 receives and reads the valid patient's ID, the measurement device 14 takes measurements of one or more vital parameters, e.g. SPO2, temperature, blood pressure. The device BCU 40 sends the measurements via BCU 26 to the measurement memory 24. In one embodiment, the measurement device BCU 40 sends the measurements and associated patient's ID via the patient BCU 26 to the measurement memory 24 as one packet of data. In another embodiment, the gateway device BCU 78 associates the measurement results with the patient's ID contemporaneously as the measurement results and patient's ID are communicated from the measurement memory 24.

If the ID reader 84 does not receive the valid patient's ID, the measurement device 14 takes measurements of one or more vital parameters which are displayed locally only. In this manner, only the measurement results values for known identities are transmitted. Accidental users, e.g. guests, can also use the measurement device but only with local display of the measurement results to prevent invalid measurements to be transmitted to the remote station. In this manner, the same measurement device can be used by multiple users such as in a family residential setting, communal living arrangements, such as retirement homes, care assistance living centers, and the like.

Because BSN communications use the patient's body as a communication link and are only receivable within about 10 cm of the patient, encryption may not be necessary at the BCU level. However, even on the BCU level, encryption provides more assured security. For data communications by radio frequency (RF), infrared (IR), and other media that can be intercepted surreptitiously, encryption is recommended and may be required by government regulations, such as HIPAA regulations in the United States.

Figure 3:
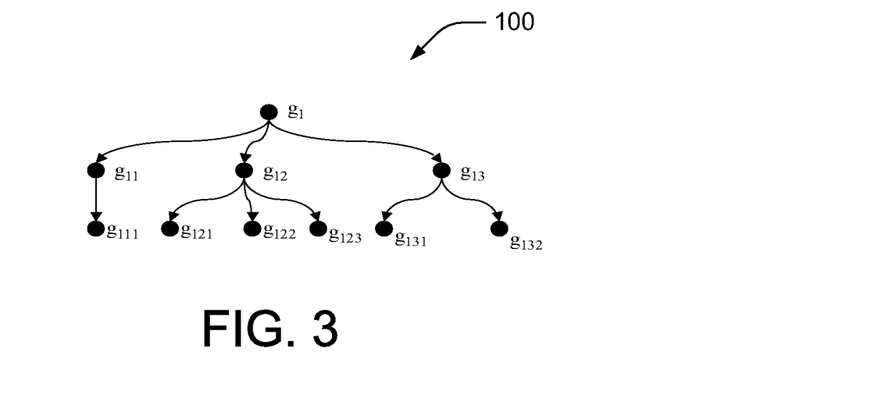
FIG. 3 illustrates a tree-structure representation for a multi-level hierarchical deployment model is illustrated.
Figure 4:
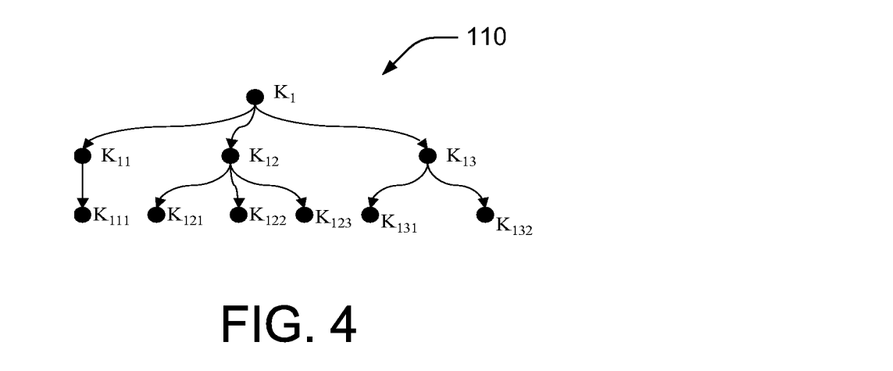
FIG. 4 is an illustration of a tree-structure representing a HKPS that employs an HRDM to enhance KPS performance on a mobile BSN.

Turning now to FIGS. 3 and 4, a hierarchical relational deployment model (HRDM) and a hierarchical key pre-distribution system (HKPS) are described, respectively, which provide a hierarchical structure to keying material, such as may be employed to securely transmit information to, from, or within the patient monitoring system 10. This allows a dedicated management of BSN security on several organizational levels, so that, for instance, individual hospitals can manage their BSN security. In parallel, secure overall interoperability is enabled, so that in emergencies all sensors manufactured by a given manufacturer can communicate with each other. In summary, HKPS provides a hierarchical infrastructure of security domain(s) (SD) to improve device identification and access control. Additionally, HKPS enables increased resiliency, full device interoperability, full device identification and thus increased overall security.

Patient monitoring for hospitals and home monitoring is primarily enabled by BSNs. A BSN is a particular wireless ad hoc network composed of nodes, such as wireless sensors attached to a patient's body and wireless medical devices in close vicinity. According to an embodiment, the patient monitoring system 10 is a BSN, including the measurement device 14, the patient identification device 20, the gateway device 72, the remote station 82, etc. In another embodiment, the patient monitoring system 10 is a portion of a larger BSN. In yet another embodiment, the BSN is a network of monitoring devices, sensors, remote stations, workstations, and the like, coupled together via wireless (and/or wired) communication channels in one or more hospitals.

In accordance with some embodiments, the HRDM is employed to model node deployment and node relationships in target networks (e.g., hospital BSNs, home BSNs, etc.). The HKPS is then employed to maximize key pre-distribution system (KPS) performance in WSNs. For instance, hospital and home BSNs are composed of mobile wireless nodes, such that each BSN is comprised of a set of nodes whose membership may dynamically vary. In both hospital and home BSNs, a BSN may be composed of a variable number of nodes and may proceed from different locations.

KPSs employed in constructing the HKPS can include one or more of deterministic pairwise key pre-distribution schemes (DPKPS), keying material schemes such as are described by Blundo et al. (See, e.g., "Perfectly Secure Key Distribution for Dynamic Conferences," CRYPTO, 1992: 471-486), private key encryption protocols, public key encryption protocols, single-key encryption protocols, polynomial-key encryption protocols, random key distribution, etc., without being limited thereto. In one embodiment, different levels of the HRDM are assigned different types of keying material. For instance, a first level may employ DPKPS keying material, a second level may employ Blundo-type keying material, and so on. Accordingly, the hierarchical protocols described herein facilitate designing a hierarchical KPS for hospital and home BSNs, improving access control service and device identification, and enhancing overall security.

Referring now to FIG. 3, a tree-structure representation for a multi-level hierarchical deployment model 100 is illustrated. Before formally defining the deployment model for a mobile BSN, its behavior may be exhibited by means of an example, such as home monitoring. For instance, a set of all sensor nodes (ECG, $SPO_2$, temperature, heart rate, respiration rate, weight, or any other health-related parameter that can be sensed or otherwise monitored, etc.) may be considered in the following example, wherein a manufacturer sells the sets of sensor nodes as a family pack. Such a family pack includes a set of sensor nodes for each family member, which enables individualized continuous monitoring at home. On the one hand, all manufacturer sensor nodes can be interoperable, since any given node may move to any given location (e.g., a heart rate sensor can be used in an emergency case by a third party, etc.). On the other hand, sensor nodes can be used consistently by a single person. That is, each family member has his or her own sensor set, but other members of the family might use a device or sensor in the set.

To facilitate providing a BSN in a family's home monitoring environment, a hospital or other healthcare environment, or a network of hospitals or the like, several conditions are satisfied by the hierarchical protocols and models described herein. Firstly, full connectivity is provided between nodes, since the nodes are mobile and any pair of nodes may potentially meet. Secondly, communications between sensor nodes belonging to different family members are probable, and therefore supported. Thirdly, nodes in the network are distributed in a hierarchical manner, such that each sensor node in the network is identified as belonging to: (a) the manufacturer, (b) a family, and (c) a family member. The three foregoing conditions, namely, full connectivity, communication likelihood, and hierarchical infrastructure, are satisfied and supported by the deployment model.

From the above example, a hierarchical relational deployment model for mobile BSN is constructed, which describes a likelihood that a given node will communicate with any other node based on node relationships, rather than on permanent location information. The model is meaningful for both static and mobile BSNs, because it is a function of the relationship between nodes rather than of the final deployment positions of the nodes.

The HRDM 100 is a deployment model in which each node in the network is classified according to an L-level hierarchical framework, which is generated by a processor and/or stored in a machine-readable storage medium or memory. That is, in this infrastructure, each node belongs to L different groups, each group at a different level in the hierarchical structure. At the highest level, all nodes belong to the same group, $g_1$. In general, nodes belonging to a group at level l are divided into several sub-groups at level l+1. Given a group at level l identified by $g_{index}$ and composed of a number $n_{index}$, of sub-groups at level l+1, the sub-groups of $g_{index}$ are named as $g_{index||i}$, with i=1, ... $n_{index}$. By using this group naming convention, given a group identifier, $g_{index}$, it is possible to know the upper groups to which this group belongs. The model 100 is represented by a tree-structure, where the highest group is the tree's root, and the leaves of each node are the sub-groups included in the group. If the model 100 is applied to the home monitoring example described above, all "manufacturer" nodes belong to $g_1$ at the highest level. At level 2, there are three groups $g_{11}$, $g_{12}$, $g_{13}$, etc. that correspond to three different families. At level 3, we see that each family is composed of a number of members (e.g., the second family, $g_{12}$, has three members, $\{g_{121}, g_{122}, g_{123}\}$, etc.).

Since each node in a BSN is classified according to the L-Level HRDM, which is classified according to the relationship between nodes, the closer the relationship between two nodes is, the higher the probability this pair of nodes will establish a communication. In general, $p_l$ may be defined as the probability of a node (i) to be in its group vicinity at level L, and (ii) not to be in its group vicinity at level l+1. Hence:

$$0 \le p_1 < p_2 < ... < p_l < ... < p_L < 1$$

$$\sum_{l=1}^{L} p_l = 1$$

According to a few examples, a given set of sensors can monitor the vital signs of the same person P from family F (e.g., with probability $p_2$=0.95). It may happen (e.g., with a probability $p_2$=0.049) that a member PP of the same family F uses one of devices of P. In another example, a device of P might be used by a person of another family with a probability $p_3$=1−$p_1$−$p_2$.

Thus, in the L-level hierarchical deployment model for BSN, each node belongs to L hierarchical groups fulfilling following conditions: the closer the relationship between two nodes is, the deeper their deepest common group is; the deeper their deepest common group, the higher the likelihood of establishing a communication; the higher the likelihood of establishing a communication, the closer the relationship between two nodes is. In general, if a node can be classified according to the HRDM, accurate prediction of the likelihood of two nodes to establish a communication can be made, and a trust-level between nodes can be discovered.

FIG. 4 is an illustration of a tree-structure representing a HKPS 110 that employs an HRDM to enhance KPS performance on a mobile BSN. A HKPS is a KPS that makes use of one or a combination of KPS to build a hierarchical architecture of security domains (SD) according to the HRDM. In this architecture, each KPS block corresponds to a SD that identifies a group of the HRDM.

According to an example, it may be desirable to secure the sensors that comprise the HRDM of FIG. 3. This can be achieved using a simple KPS and/or a HKPS and a network-wide key. In this KPS, all devices that belong to the same SD carry the same key. In the first approach, the KPS (and network-wide key) alone are employed, wherein all of a manufacturer's sensors worldwide share the same network wide key $K_1$. If a node is captured or otherwise compromised, all communications are compromised. For example, if an intruder captures the heart rate sensor from another member of family 3 (see FIG. 3), the intruder can listen to all communications. However, in the second approach, the HRDM of FIG. 3 is employed to create a HKPS. In this approach each group $g_{index}$ is assigned a different key $K_{index}$. Thus, all sensors of a given manufacturer can communicate with each other by using the key $K_1$ at the highest level ($g_1$), so that full interoperability is ensured. A given manufacturer's nodes belonging to the same family also share a key at the second level. Finally, each set of devices for each family member share a key at level 3. In this manner, if an intruder captures a device, the intruder does not gain information about the key of other members.

In accordance with one embodiment, hierarchical infrastructure of security domains facilitates improving device identification (according to the different hierarchical SDs) as well as providing a mechanism to control access to different SDs. According to another embodiment, each node has keying material from each of L independent SDs. Because the HRDM nodes communicate by using keying material at the deepest level, the model includes a smaller number of nodes than would be necessary using conventional approaches. Yet another embodiment provides for decrementing the keying material to update in case of an attack. For instance, if an attack against a SD at the deepest level takes place, only the deepest level of the SD is damaged, while rest of the SD remains secure.

Figure 5:
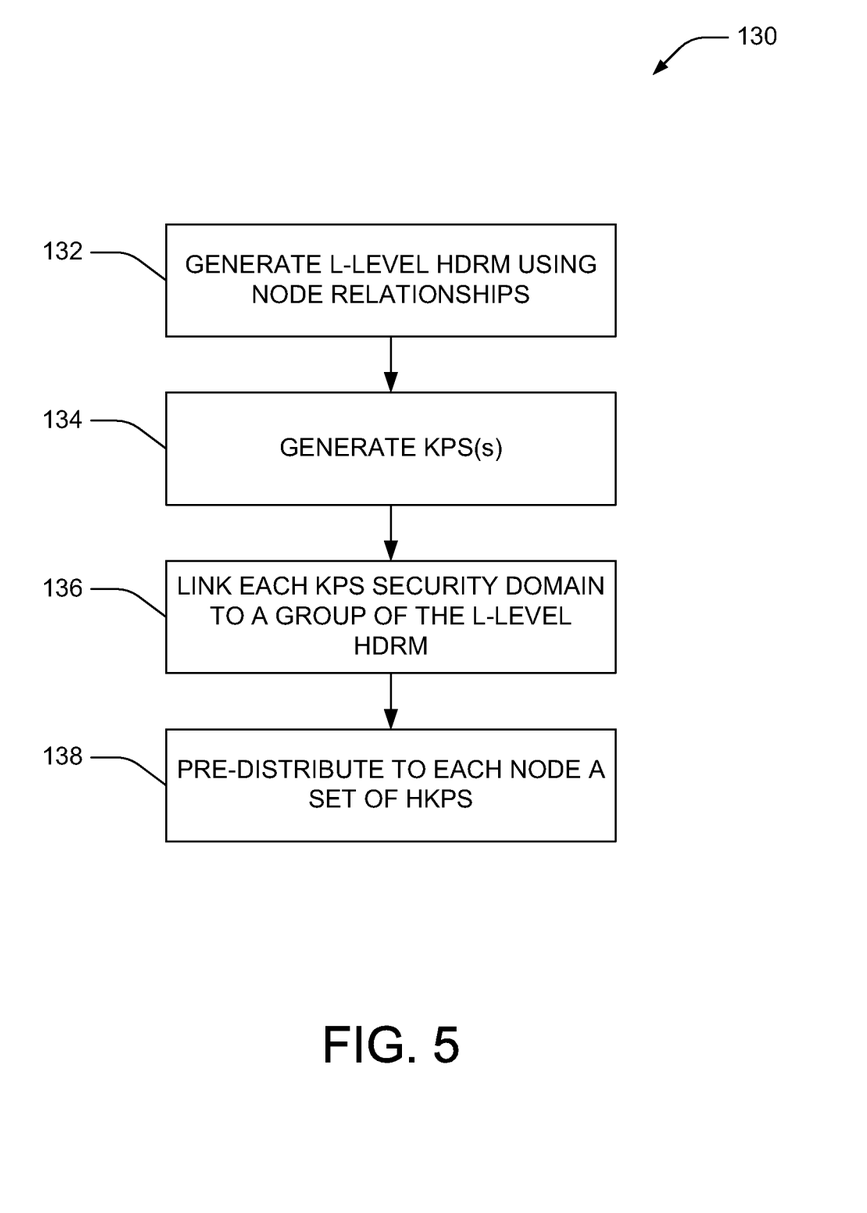
FIG. 5 illustrates a method for constructing a HRDM and pre-distributing keying material to nodes in a BSN.

FIG. 5 illustrates a method 130 for constructing a HRDM and pre-distributing keying material to nodes in a BSN. The method can be performed before network deployment and in a secure environment, as desired. Additionally, the method 130, as well as the methods of the following figures, may be executed by a dedicated processor and/or a setup server (not shown), or the like, and may be stored as machine-readable instructions in a memory or the like.

At 132, an L-level HRDM is created as a function of node relationships. At 134, one or more KPSs are generated. Each KPS has a security domain that is linked to a group within the HRDM, at 136. At 138, a set of HKPS is distributed to each node. Each set of HKPS is composed of L subsets of keying material, each subset corresponding to a KPS security domain.

For example, a number of nodes that are present in a hospital or healthcare environment can be identified, and a KPS for each group of nodes can be generated. Such nodes include, for instance, patient monitor devices, sensors for measuring a parameter such as a temperature, weight, $SPO_2$, heart rate, blood pressure, respiratory rate, etc., patient or employee identification sensors, or any other type of suitable or desired sensor. In one embodiment, the nodes are grouped according to the hospital in which they are employed, and a KPS is generated and assigned at the hospital level. Nodes are then sub-grouped according to the hospital departments or wards in which they are primarily employed (e.g., maternity, cardiac, neonatal, emergency room, etc.). A department-level KPS is then generated and assigned to the subgroups. Each department subgroup can be further divided according to individuals employing the node sensors (e.g., an employee who regularly uses the sensors, a patient to whom the sensors are attached, etc.). A KPS for the individual level is generated and assigned to these subgroups as well.

Figure 6:
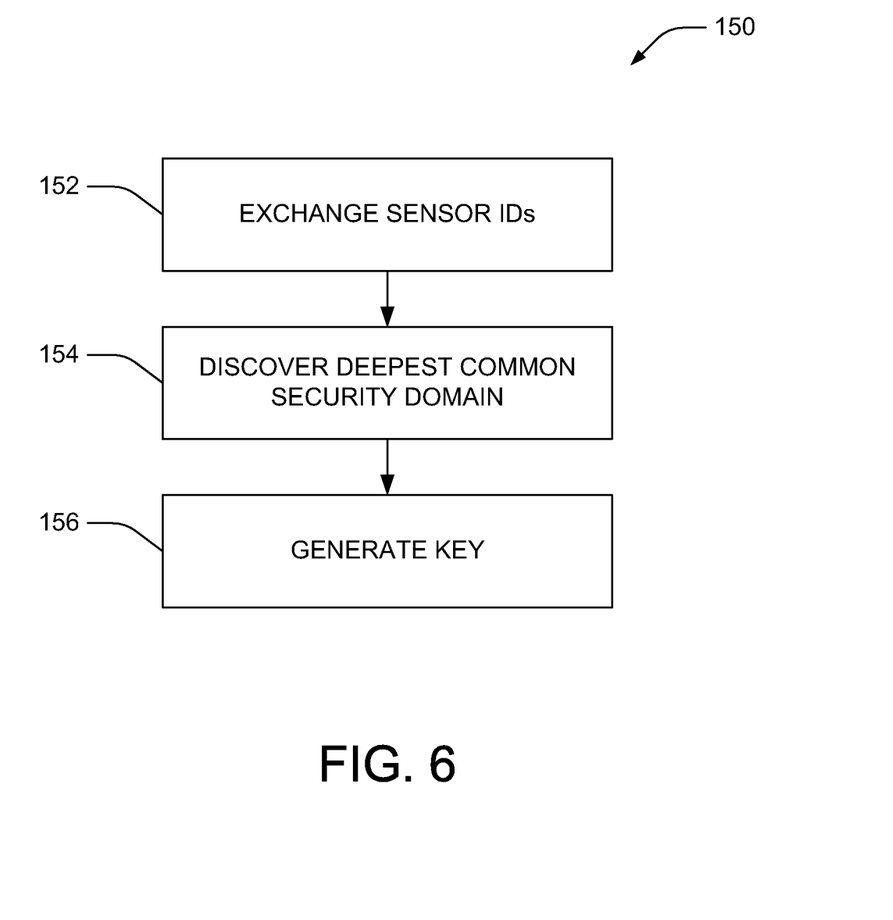
FIG. 6 illustrates a method for executing an operational phase of the hierarchical protocol, after node deployment, such as when two nodes are brought into proximity with one another and begin a handshake protocol to agree on a key for further communication.

FIG. 6 illustrates a method 150 for executing an operational phase of the hierarchical protocol, after node deployment, such as when two nodes are brought into proximity with one another and begin a handshake protocol to agree on a key for further communication. At 152, two proximate nodes exchange node IDs. That is, nodes (e.g., sensors or other network devices) exchange node ID information, which includes information pertaining to the security domain to which the node belongs and keying material employed by the security domain. At 154, the nodes discover their deepest common node and security domain, which offers a highest relative security level. At 156, nodes exploit keying material at the deepest common security domain to agree on a common key. Key agreement protocol is executed according to the specification of the chosen KPS.

For instance, sub-grouped nodes can communicate with other nodes in their subgroup using the keys assigned to the subgroup by the subgroups KPS. Nodes that are not in a common subgroup can communicate using the keys assigned by the KPS of the first parent node common to the nodes attempting to communicate. For instance, nodes in a common department subgroup but in different individual subgroups can communicate using the keys of the KPS assigned to their department, while nodes in different department subgroups communicate using keys provided by the hospital-level KPS.

In another example, each hospital has its own KSP, to provide heightened security to patients whose data is stored in the nodes and communicated thereby. Such a precaution facilitates preventing a party from stealing a node from a first hospital and employing the node to retrieve confidential information from the network in a second hospital. Additionally, if desired, an override function can be built in to each node to permit a nurse, physician, or the like to override the security feature and permit a node from a first hospital to communicate with nodes and/or the network of a second hospital. In one embodiment, the override function provides new keying material to the node to permit it to communicate in the new environment. For instance, in an emergency situation where a patient that is moved from a first hospital (or home) to a second hospital, with vital sign monitoring nodes attached to the patient or otherwise carrying information that is useful to medical personnel at the second hospital, the medical personnel can override the security feature and permit communication between the foreign node(s) and the second hospital's nodes.

Figure 7:
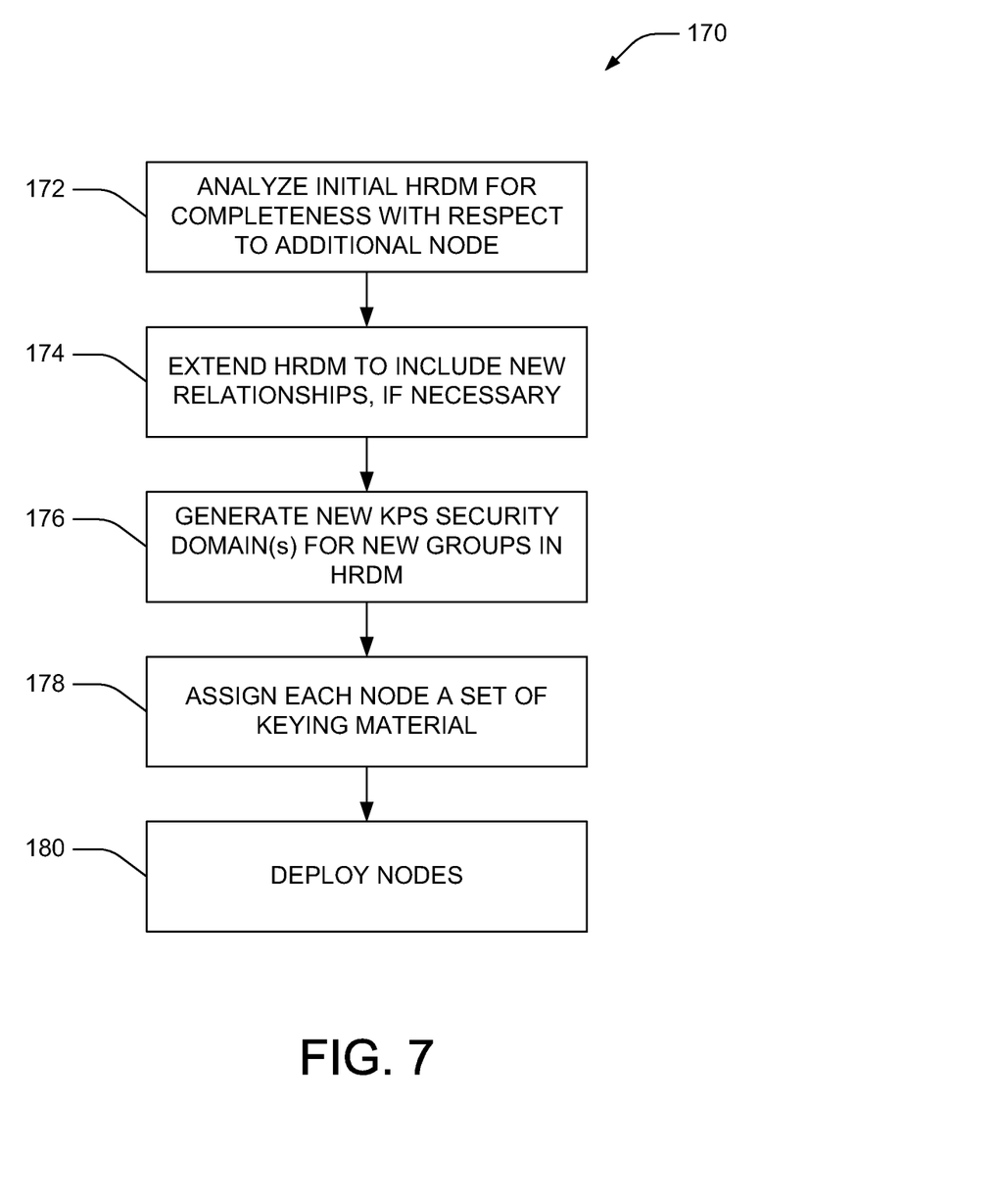
FIG. 7 is an illustration of a method for adding a new node to an existing hierarchical model.

FIG. 7 is an illustration of a method 170 for adding a new node to an existing hierarchical model. At 172, an initial HRDM, such as can be generated via method 130, is analyzed to determine whether it represents relationships with a newly introduced node. If the initial HRDM does not represent such relationships, then at 174, the HRDM is extended and/or reorganized to include the new node and its relationships with other nodes (e.g., manufacturer, family, member, etc.). One or more new KPS security domains is/are generated, at 176, for any new groups in the extended HRDM. At 178, each node is assigned a set of keying material. The nodes are then deployed, at 180.

For instance, a "new" device that attempts to communicate with a second device in a group or subgroup of the HRDM is identified to determine if it has previously been accounted for in the HRDM. If the new device was previously accounted for in the HRDM but powered off for a time, during which the HRDM has changed (e.g., other new devices have been introduced, causing a change in the HRDM), then the HRDM is reorganized to include the new device. In a related example, the new device is entirely new to the network, and the HRDM is reorganized accordingly. Alternatively, if the new device is powered up and previously integrated into the HRDM, and if no changes have occurred in the HRDM, then the new device can proceed with a handshake protocol to communicate with the second device using keys provided by the KSP of the lowest common level to both devices (e.g., individual, department, hospital, manufacturer, etc.)

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A method for measuring health related parameters of least two patients, comprising:

sending, by a patient identification device, an identification for each of the at least two patients to a measurement device;

receiving and reading a valid identification for at least one of the at least two patients and measuring, with the measurement device, a health related parameter of the at least one of the at least two patients having a valid identification;

communicating the health related parameter measurement results of the patient having a valid identification from the measurement device to the patient identification device carried by the patient via body-coupled communication;

communicating the measurement results separately and concurrently with a patient identification code from the identification device to a gateway device via body-coupled communication;

associating, via the gateway device, the health related parameter measurements with the separately and concurrently received patient identification code as the health related parameter measurements and patient identification code are received at the gateway device, the association between the measurement results and the patient identification code by the gateway device being a first electronic association between the measurement results and the patient identification code;

receiving and reading an invalid identification for the other patient of the at least two patients and measuring, with the measurement device, a health related parameter of the other patient of the at two patients having an invalid identification; and displaying the measurement results for the other patient having an invalid identification locally on the measurement device.

2. The method as set forth in claim 1, wherein the patient identification device includes a measurement memory and further including:

storing the measurement results in the measurement memory.

3. The method as set forth in claim 1, wherein the measuring unit includes a sensor and further including:

measuring a physiological function of the patient.

4. The method as set forth in claim 1, further including:

assigning measurement devices to one or more patients, each measurement device being encoded with an electronic device identification code that uniquely identifies the selected patient which it is assigned to;

communicating the electronic identification code of the measurement device to a measurement memory contemporaneously with communicating the measurement results; and associating the communicated measurement results with the patient via the electronic identification code of the measurement device.

5. The method as set forth in claim 1, further including:

assigning a patient identification device to the patient which identification device is encoded with an electronic patient identification code that uniquely identifies the patient which it is assigned to;

communicating the patient identification code to the gateway device contemporaneously with the communicating the measurement results; and associating the communicated patient identification code with the communicated measurement results.

6. The method as set forth in claim 1, further including:

establishing a wireless body-coupled communication link when the patient is within approximately 10 cm of the measurement device or touching the measurement device; and establishing a wireless body-coupled communication link when the patient is within approximately 10 cm of the measurement device or touching the gateway device.

7. The method as set forth in claim 1, further including:

assigning measurement devices to selected patients;

assigning a patient identification device to each patient, which each patient identification device is encoded with an electronic patient identification code that uniquely identifies the patient which it is assigned to;

communicating the patient identification code to the measurement device; and associating the communicated patient identification code with the communicated measurement results.

8. The method as set forth in claim 1, further including generating a hierarchical relational deployment model (HRDM) including a tree structure of nodes representing one or more devices or sensors.

9. The method as set forth in claim 8, further including generating multi-level hierarchical key pre-distribution scheme (HKPS) and assigning unique keying material to each of a plurality of levels in the HKPS.

* * * * *